United States Patent
Bonzagni et al.

(12) 
(10) Patent No.: US 6,327,787 B1
(45) Date of Patent: Dec. 11, 2001

(54) GLOVE FITTING DEVICE AND METHOD

(75) Inventors: Maria Bonzagni, W. Bridgewater; Saunders N. Whittlesey, Deerfield, both of MA (US)

(73) Assignee: Acushnet Company, Fairhaven, MA (US)

(*) Notice: Subject to any disclaimer, the term of this patent is extended or adjusted under 35 U.S.C. 154(b) by 0 days.

(21) Appl. No.: 09/494,646

(22) Filed: Jan. 31, 2000

(51) Int. Cl.$^7$ ............................................. A61B 1/00
(52) U.S. Cl. .............................. 33/512; 33/2 R; 33/549
(58) Field of Search ................... 33/512, 2 R, 17 R, 33/755, 756, 759, 760, 494, 511, 514.2, 515, 549

(56) References Cited

U.S. PATENT DOCUMENTS

| | | |
|---|---|---|
| 587,940 | 8/1897 | De Lisle . |
| 740,943 * | 10/1903 | Summersby et al. .................. 33/2 R |
| 806,531 | 12/1905 | Engelhardt et al. . |
| 1,331,823 | 2/1920 | Phillips . |
| 1,430,794 | 10/1922 | Canfield . |
| 1,997,920 | 4/1935 | Bliss . |
| 2,078,368 | 4/1937 | Brannock . |
| 2,146,799 | 2/1939 | Davis, Jr. ............................... 33/512 |
| 2,176,288 | 10/1939 | Baird et al. ............................. 33/2 R |
| 2,200,223 | 5/1940 | Brown . |
| 2,592,188 | 4/1952 | Rosenberg et al. . |
| 2,605,548 | 8/1952 | Clarke . |
| 3,018,554 | 1/1962 | Roberson . |
| 4,115,873 | 9/1978 | Stansbury . |
| 4,160,327 | 7/1979 | Martin et al. . |
| 4,173,074 | 11/1979 | Newman et al. ....................... 33/2 R |
| 4,360,972 | 11/1982 | Montgomery ......................... 33/17 R |
| 4,395,826 | 8/1983 | Bidegain et al. . |
| 4,897,924 | 2/1990 | Tepley .................................... 33/512 |

FOREIGN PATENT DOCUMENTS 33495 11/1885 (DE) .

* cited by examiner

Primary Examiner—Christopher W. Fulton
(74) Attorney, Agent, or Firm—Pennie & Edmonds LLP

(57) ABSTRACT

The present invention relates to a glove fitting device and method for measuring aspects of a user's hands and recommending an appropriate glove size therefrom. The device includes a platform with left-hand and right-hand measuring stations. Each measuring station includes at least one measuring system comprising a plurality of cooperating elements, such as scales, to measure the length of at least two of a user's digits and selecting a preferred finger length value. Each of the two digits is measured, relative to a different position. The device further includes a measuring tape that allows a girth value to be obtained of user's palm. In addition, the device includes a sizing grid that allows the preferred finger length value and the girth value to be correlated with a recommended glove size.

26 Claims, 7 Drawing Sheets

Finger Lengths

| Palm Sizes | 1 | 2 | 3 | 4 | 5 | 6 | 7 | 8 | 9 |
|---|---|---|---|---|---|---|---|---|---|
| 0 | Women's S | Women's M | Women's ML | | | | | | |
| 1 | Women's M | Women's M | Women's ML | Women's ML | | | | | |
| 2 | | Women's ML | Women's ML | Women's L | | | | | |
| 3 | | Women's L | Women's L | Women's L | | | | | |
| 4 | | Cadet S | Cadet S / Men's S | Men's S | Men's S | Men's M | | | |
| 5 | | | Cadet M | Men's M | Men's M | Men's M | Men's ML | | |
| 6 | | | | Cadet ML | Cadet ML / Men's ML | Men's ML | Men's ML | | |
| 7 | | | | | Cadet L / Men's L | Men's L | Men's L | | |
| 8 | | | | | | Cadet XL / Men's XL | Men's XL | Men's XL | |
| 9 | | | | | | | | Men's XXL | Men's XXL |

*Fig. 9*

GLOVE FITTING DEVICE AND METHOD

FIELD OF THE INVENTION

The present invention relates to a glove fitting device and method for measuring aspects of a user's fingers and hands and recommending an appropriate glove size based on the measurements.

BACKGROUND

In order to provide comfortable fitting gloves for different users who have a variety of hand shapes and sizes, manufactures generally provide consumers with a variety of different sized gloves. With respect to athletic gloves, such as those used in golf, proper glove fit is necessary for an additional reason. In such gloves, proper fit ensures that the glove does not interfere with the feel of a sports implement in the user's hands. Generally, gloves are produced in three size classifications, such as women's, men's, and cadet. Additionally, gloves within each size classification are usually produced in further size classifications, such as small, medium, large, extra-large, etc. Thus, retail locations often display a large number of different glove sizes and a customer often faces a time-consuming task of trying on multiple gloves in order to identify gloves with the best fit.

A number of hand measuring instruments have been attempted. None, however, provide a straightforward system that rapidly measures essential aspects of a customer's hand and accurately utilizes the measurements to suggest a glove size. For example, U.S. Pat. Nos. 1,997,920; 2,176,288; 2,605,548; and 4,173,074 disclose devices that measure palm width and the length of only the longest finger. Although such devices that measure the length of only a single finger and palm width may provide ease of use, these devices do not provide sufficient or accurate information to allow accurate prediction of the customer's glove size.

Other references, such as U.S. Pat. Nos. 587,940 and 2,146,799 disclose devices that measure the girth of a hand and measure the length of the longer finger or fingers. For many individuals, however, these measurements also may not be sufficient to accurately predict the customer's glove size.

Several references, such as DT33495 and U.S. Pat. No. 4,897,924 disclose devices that measure the length of all of the fingers. Although these devices provide additional absolute information about the dimensions of a hand, such devices are generally too complicated and cumbersome to be used effectively in a retail setting.

Thus, a glove fitting device and method are needed that are easy for a customer to use in a retail setting, that allow pertinent aspects of their hands to be measured, and that more accurately predict their glove size.

SUMMARY

The present invention includes a hand measuring device for determining a glove size for a user with five digits. The device includes a platform and at least one measuring station associated with the platform. The measuring station includes a girth scale operatively associated with the platform for measuring a user's palm girth value and first and second measuring systems. The first measuring system measures a first digit length value of a first digit of a user's hand. The second measuring system measures a second digit length value of a second digit of the user's hand.

In one embodiment, the device includes at least two measuring stations. One measuring station measures the user's right hand and the other measuring station measures the user's left hand.

In yet another embodiment, the first digit length value is measured relative to a first position and the second digit length value is measured relative to a second position. The first position and the second position are located different distances from a reference point.

In another embodiment, the first and second measuring systems include separate scales with a plurality of spaced marks. A single scale can also be used as the measuring systems.

In addition, in one embodiment the first digit is the index finger and the second digit is the middle finger.

Furthermore, in one embodiment a grid associated with the platform for correlating a plurality of palm girth values and a plurality of preferred finger length values with a plurality of predetermined glove sizes.

The present invention also includes a method for fitting gloves to the user that includes the steps of measuring at least one hand of the user on a first scale to determine the girth of a palm of the user and assigning a girth value to that measurement. The method also includes the step of measuring the length of a first digit of at least one hand on a second scale and assigning a first digit length value to that measurement. In addition, the method includes the step of measuring the length of a second digit of at least one hand on a second scale and assigning a second digit length value to that measurement, selecting the largest of the first digit length value or the second digit length value as a preferred digit length value, and recommending to the user a predetermined glove size based on the preferred digit length value and the girth value.

In another embodiment, two hands can be measured and the longest preferred digit length values and girth values can be used to recommend the predetermined glove size.

In one embodiment, the step of recommending further includes recommending to the user a women's glove size, if the girth value is three or less. Alternatively, recommending to the user a cadet or men's glove size, if the girth value is greater than four.

BRIEF DESCRIPTION OF THE FIGURES

Preferred features of the invention may be further understood by reviewing the following detailed description in conjunction with the appended drawing figures wherein:

FIG. 9 is a top view of a sizing grid according to the present invention.

DETAILED DESCRIPTION OF THE PREFERRED EMBODIMENT

Figure 1:
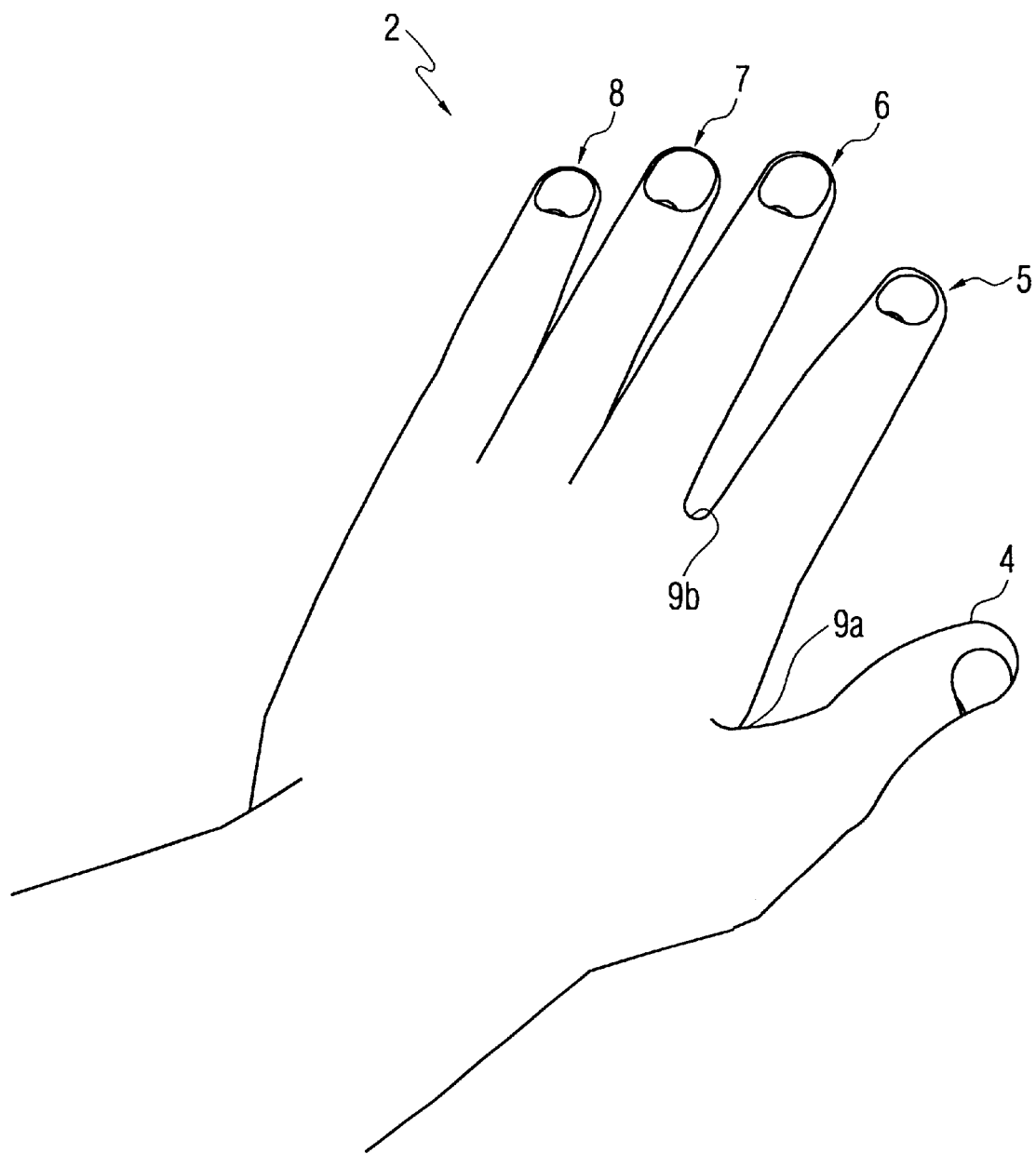
FIG. 1 is a perspective view of a typical human hand.

Referring to FIG. 1, a typical human hand 2 comprises five digits including a thumb 4 and four fingers 5–8. Beginning with the thumb 4, and proceeding laterally across the hand, the five digits as used in the specification and claims are referred to as the thumb 4, index finger 5, middle finger 6, ring finger 7, and little finger 8. Crotches, such as 9a and 9b are located between each of the digits at the connection between adjacent digits.

Figure 2:
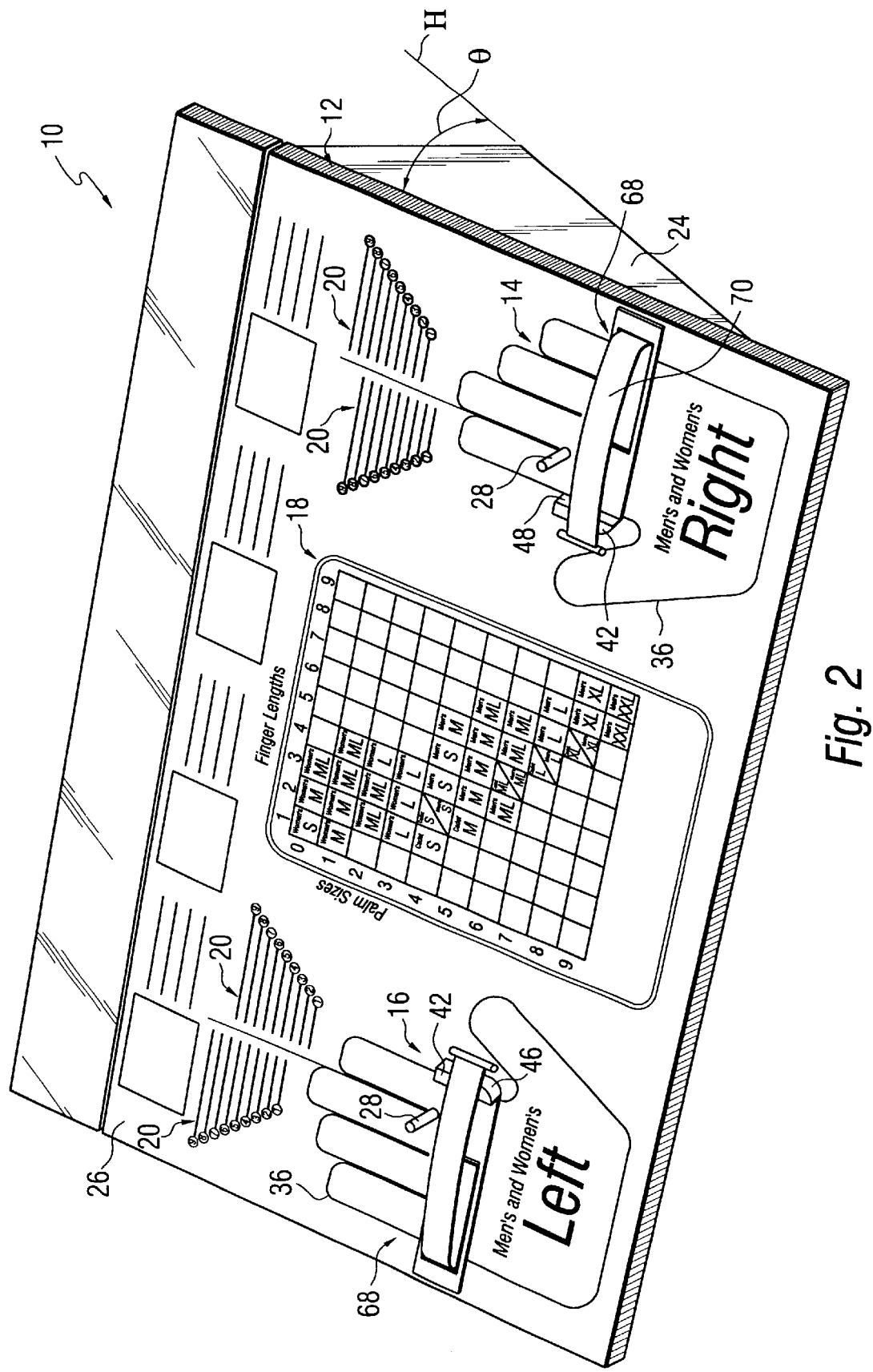
FIG. 2 is a perspective view of a glove fitting device according to the present invention.

Referring to FIG. 2, a glove fitting device 10 according to the present invention is shown and includes a platform 12 with a right-hand measuring station 14, a left-hand measuring station 16, and a sizing grid 18 thereon. As described below, each measuring station 14 and 16, includes at least one measuring system 20 comprising a plurality of cooperative elements for measuring the length of at least two of the user's digits.

Platform 12 preferably is secured to the top of a support base 24. Preferably, support base 24 presents platform 12 to a user at an angle θ with respect to a horizontal line H to facilitate ease of use and proper hand positioning during use. More preferably, angle θ is between about 0°–35° and most preferably angle θ is about 20°.

The platform 12 and base 24 may be formed of plexiglass, acrylic, glass, wood, metal or any other material that provides a smooth, durable surface as required for the device 10. An upper surface 26 of the platform 12 may also include a coating, such as paint, stain, or laminate to protect elements on platform 12. In addition, the platform 12 can be formed of two or more materials, such as metal covered with plexiglass.

Figure 3:
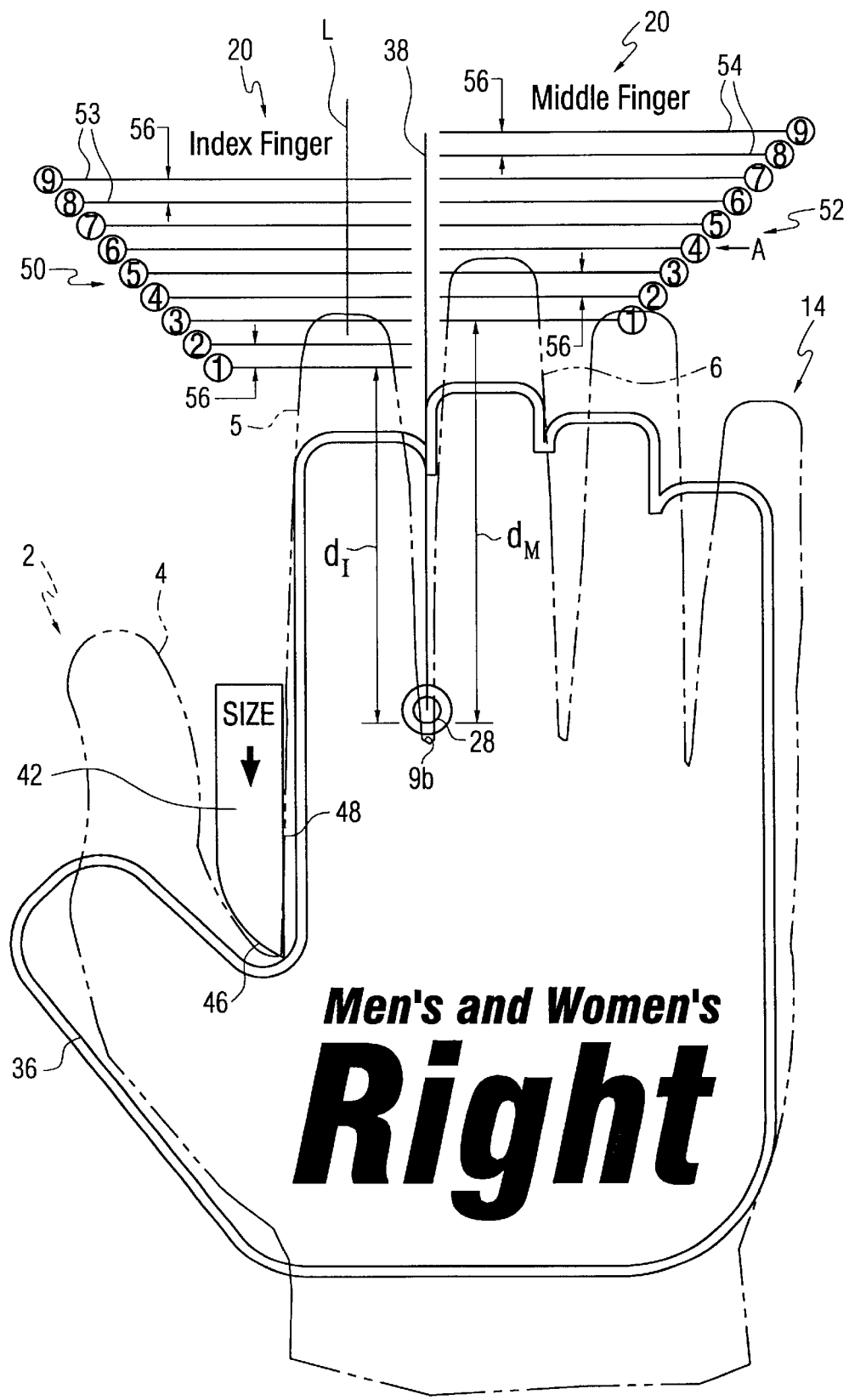
FIG. 3 is a top, schematic view of a right-hand measuring station according to the present invention.

Referring to FIG. 2, left-hand measuring station 16 is a mirror image of right-hand measuring station 14 and contains similar elements. Each hand measuring station 14 and 16 includes at least one stop member 28 configured to abut at least a portion of a crotch 9b (as shown in FIG. 3) between the index finger 5 and middle finger 6 (shown in phantom), when the user's hand 2 (shown in phantom) is placed in a proper measurement position on the hand measurement stations 14 and 16. Measuring stations 14 and 16 also include a hand outline 36 to assist the user in positioning their hand.

Referring to FIG. 3, the proper measurement position of the hand 2 (shown in phantom) placed on measurement station 14 occurs when the stop member 28 contacts the crotch 9b, and a longitudinal axis L of one finger is parallel to line 38 extending from the stop 28. This position allows finger length values and palm girth values to be obtained that are useful in selecting a glove size, as described below. Stop member 28 can be a peg, a wall-like member or any similar structure that limits the forward movement of the hand, when placed on the hand measuring station. This allows accurate finger length measurements to be taken. Similarly, stop member 28 also allows a proper lateral or side-to-side position of the hand placed on each measurement station so that accurate girth measurement can be taken, as discussed below.

Referring to FIGS. 2 and 3, the hand measuring stations 14 and 16 also include a thumb stop member 42 configured to abut at least a portion of the crotch 9a between the thumb 4 and index finger 5. Preferably, thumb stop member 42 has two vertical surfaces 46 and 48 (as best shown in FIG. 3) substantially perpendicular to the platform 12. The surfaces 46 and 48 contact the sides of the thumb 4 and index finger 5, respectively. Preferably, vertical surface 46 is curved or angled with respect to vertical surface 48 so that stop 42 conforms to the natural location of the thumb 4 and index finger 5.

In another embodiment, each hand measuring station may have additional stop members configured to abut at least a portion of another or all of the crotches between the other fingers. Thumb stop member 42 and stop member 28 alone or in combination assist to properly position a user's hand as described above. Indeed, if desired for error-minimization additional stop members may be positioned adjacent either side of a user's hand.

As best seen in FIG. 3, first embodiments of measurement systems 20 comprise an index finger scale 50 and a middle finger scale 52, respectively. Each scale 50 and 52 has a plurality of marks 53 and 54, respectively. The marks 53 and 54 are substantially perpendicular to the line 38 adjacent thereto. Preferably, scales 50 and 52 are positioned so that an index finger 5 and a middle finger 6 (shown in phantom) of hand 2 (shown in phantom), which is properly positioned against stop member 28 and thumb stop member 42 are aligned with the corresponding scale 50 or 52.

Each mark 53 and 54 of each scale 50 and 52 has labels corresponding to index finger values and middle finger values. The labels comprise sequential whole numbers from one (1) to nine (9). Thus, the scales 50 and 52 preferably have nine marks; however, scales with more or less marks can also be used, as necessary. Although labels with any sequence of any symbols, such as any numbers, letters, characters, or combination thereof could be used. In a preferred embodiment, intervals 56 or the spaces between adjacent marks 53 and 54 within index finger scale 50 and within middle finger scale 52 are equal. The intervals 56 between marks along each finger scale correspond, for example, to variations in size difference between successively sized gloves advantageously allowing the present invention to more accurately predict a user's glove size.

The scale 50 is separate from the scale 52. In another embodiment, one scale can be used instead of two.

In hand measurement station 14, identically labeled marks of index finger scale 50 and middle finger scale 52 are offset from one another relative to a distance from stop member 28, which is a reference point. Index finger scale 50 begins or is referenced to a position that is a distance $d_I$ from stop member 28. The middle finger scale 52 begins or is referenced to a position that is a distance $d_M$ from the stop member 28. It is preferred that distance $d_I$ is less than distance $d_M$, however, this is not required. As a result, the mark labeled one (1) on index finger scale 50 is disposed closer to stop member 28 than the mark labeled one (1) on middle finger scale 52. An example of this occurs, when the index finger 5 and middle finger 6 have identical absolute lengths so that they extend to a point A, the index finger value is six (6) and the middle finger value is four (4). Thus, the measurement from the index finger scale 50 is greater than the measurement from the middle finger scale 52.

Figure 4:
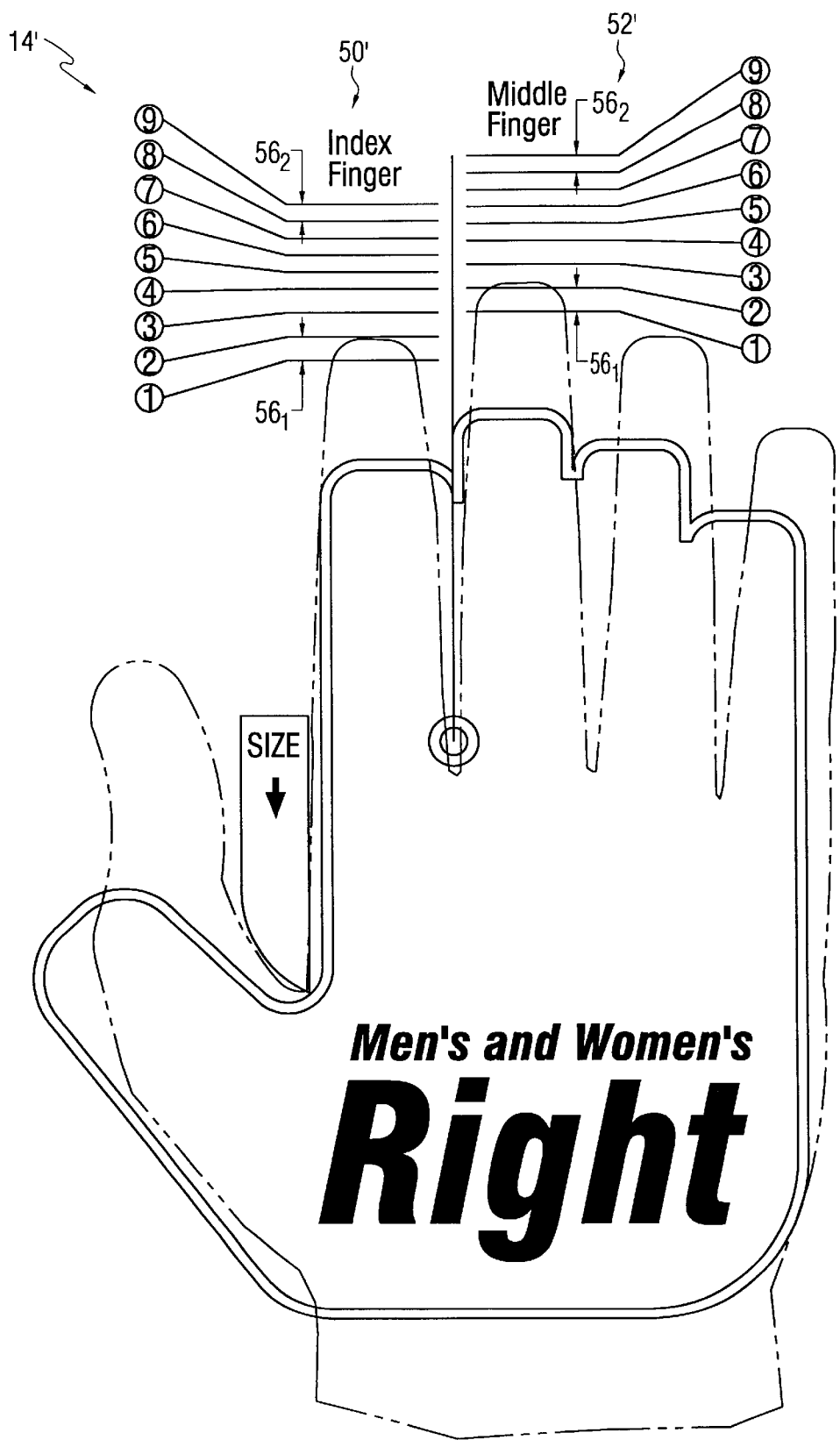
FIG. 4 is a top, schematic view of a second embodiment of the right-hand measuring station according to the present invention.

Referring to FIG. 4, another embodiment of right-hand measuring station 14' has marks 53' and 54' for scales 50' and 54'. The interval $56_1$ between adjacent marks is larger than the interval $56_2$ between other adjacent marks. In another embodiment, the intervals between marks can vary in a step-wise or gradual fashion along all or only a portion of each finger scale. Intervals $56_1$ between marks 1–2, 2–3 and 3–4 on each scale 50' and 52' are different from intervals $56_2$ between marks 4–5, 5–6, 6–7, 7–8, and 8–9. However, each interval $56_1$ is the same, and each interval $56_2$ is the same.

Although FIGS. 3 and 4 show that the intervals 56, $56_1$, and $56_2$ between adjacent marks of index finger scale 50 are similar to the intervals 56 between adjacent marks of middle finger scale 52, the intervals between adjacent marks along all or a part of the index finger scale 50 may be different than the intervals between marks along all or part of the middle finger scale 52. Such differences in the intervals between the adjacent marks would allow the glove fitting device 10 to account, for example, for differences in the relative importance of the length of one digit compared to a second digit in determining proper glove size.

Figure 5:
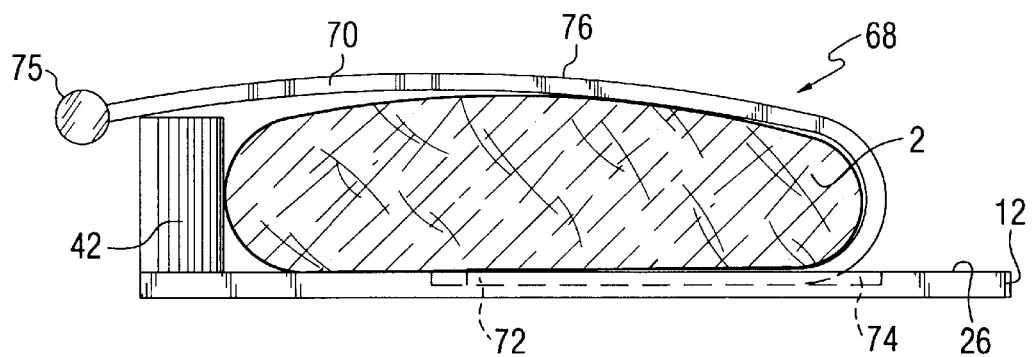
FIG. 5 is a partial, cross-sectional view of the right-hand measuring station shown in FIG. 3, with a hand disposed therein.
Figure 6:
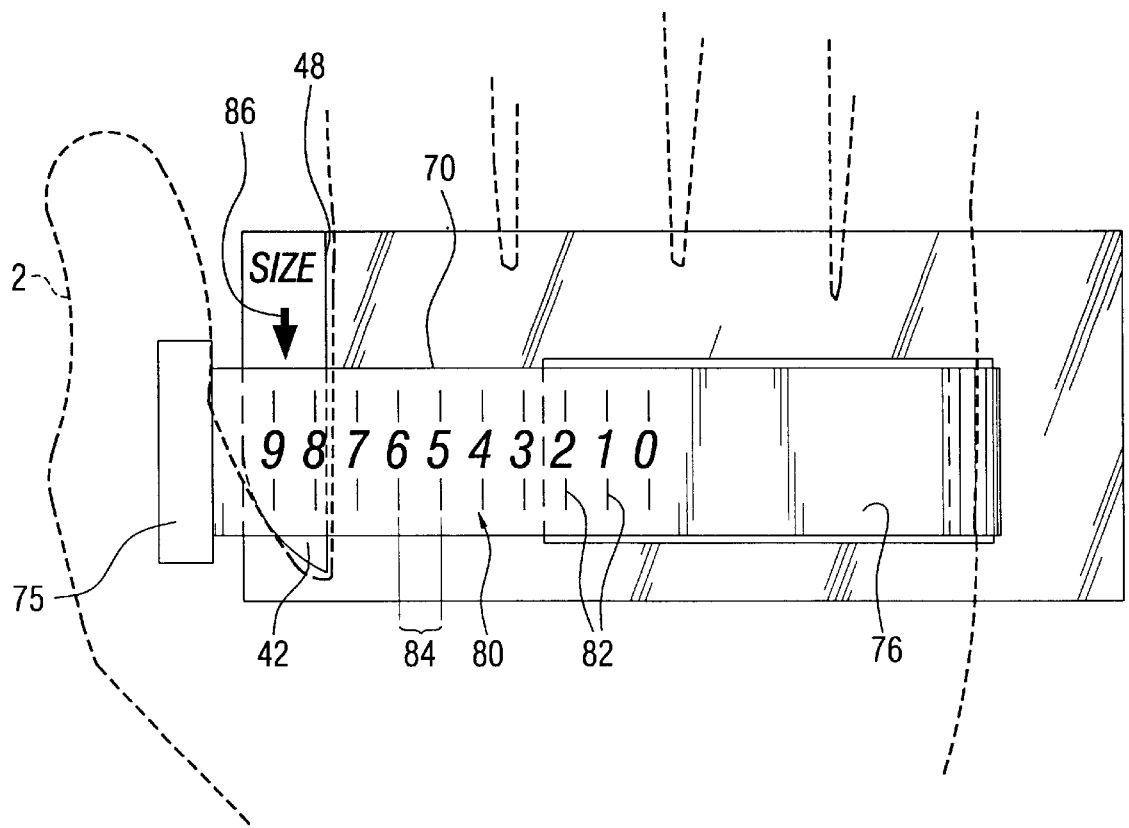
FIG. 6 is a partial, top view of the measuring station shown in FIG. 3; wherein the station is in use.

Referring to FIGS. 2, 5, and 6, each hand measuring station 14 and 16 also includes a girth measurement device 68. The girth measurement device 68 includes a strip of material or measuring tape 70 configured to allow a user to determine a girth value which is related to the girth of the hand about the palm. The strip of material 70 is positioned with respect to thumb stop 42 so that it will contact the widest part of the user's palm.

One fixed end portion 72 of measuring tape 70 is secured within a recess 74 (shown in phantom) defined in the platform 12 so that portion 72 of the tape 70 is flush with the upper surface 26 of the platform 12. Fixed end portion 72 may be permanently secured to platform 12 by, for example, adhesive, conventional mechanical fasteners, ultrasonic welding, or the like. Fixed end portion 72 may also be releasably secured to platform 12 with, for example hook and loop fasteners, a snap-like fastener or the like. The free end of the tape 70 includes a rod 75 or similar member that allows a user to easily grip the tape 70.

Referring to FIG. 6, an upper surface 76 of measuring tape 70 includes a girth scale 80 comprising a plurality of labeled marks 82 each corresponding to a girth value. Here, the upper surface 76 of measuring tape 70 is the surface of tape, which is visible to the user with the tape in the use or measurement position. The marks 82 are labeled with the girth values in sequential whole numbers zero (0) to nine (9). Thus, the scale 80 preferably has ten marks; however, a scale with more or less marks can also be used, as necessary. In addition, other symbols can be used to label the scale 80, as discussed above. The intervals 84 or spaces between adjacent marks 82 are substantially constant. However, the intervals 84 along all or a portion of the girth scale may vary to allow the measured girth value to account for differences between successive size gloves, as discussed above with respect to the finger scales.

Thumb stop 42 has a reference mark 86 thereon to indicate which girth value on the girth scale 80 should be noted by the user. The selected girth value is the labeled mark 82 of girth scale 80 most closely aligned with reference mark 86, when tape is drawn about the hand 2 (shown in phantom). Alternatively, vertical wall 48 of thumb stop 42 may serve the reference similar to reference mark 86.

Figure 7:
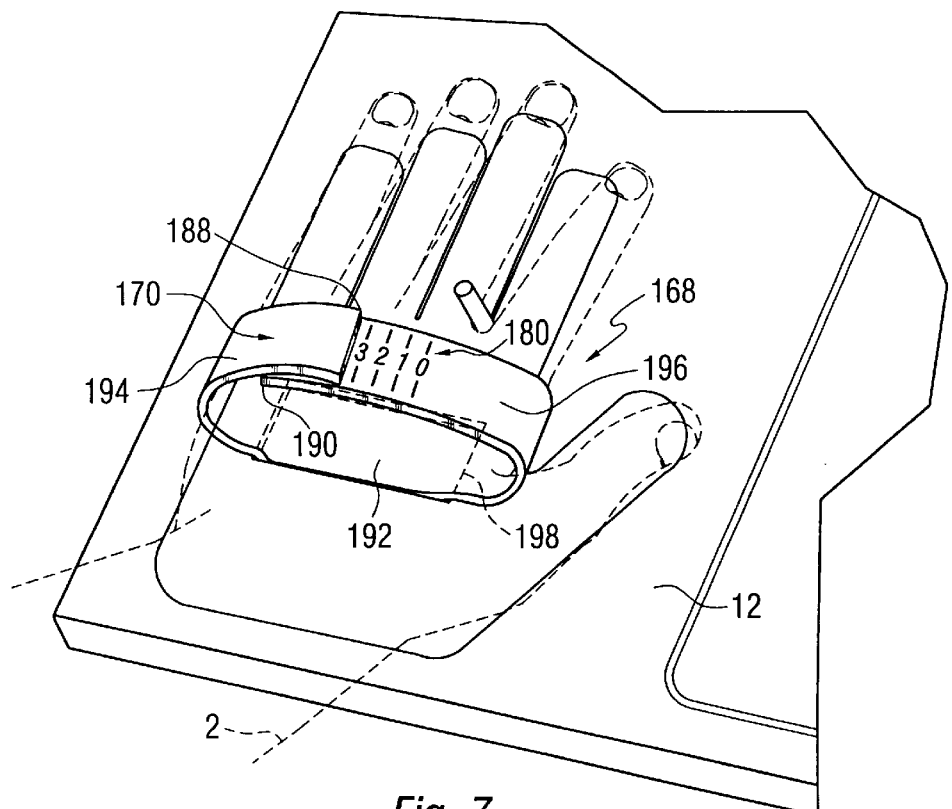
FIG. 7 is a partial, perspective view of a third embodiment of a left-hand measuring station according to the present invention.

Turning to FIG. 7, a second embodiment of the girth measurement device 168 is shown. The girth measurement device 168 includes measuring tape 170 with a first free end 188 and a spaced, second free end 190. A central portion 192 of measuring tape 170 is spaced apart from first free end 188 and second free end 190, and fixed to the platform 12. Thus, two free portions 194 and 196 of the tape are defined. The free portion 194 lies between the central fixed portion 192 and the free end 188. The free portion 196 lies between the central fixed portion 192 and the free end 190. Central fixed portion 192 is configured to lie beneath at least a portion of the user's hand 2 (shown in phantom), when the hand is placed upon the measuring station. Central fixed portion 190 is disposed within a recess 196 (shown in phantom), but also may be located on top of the platform 12 upper surface. A girth scale 180 is located on the upper surface of free portion 196.

In use, a user draws portion 196 over the back of their hand 2 and overlies portion 194 on portion 196. The free end 188 aligns with the girth value on the scale 180 to be selected. As an alternative, the measuring tape 170 can be formed of two strips of material that form the portions 194 and 196 instead of a single piece of material.

Figure 8:
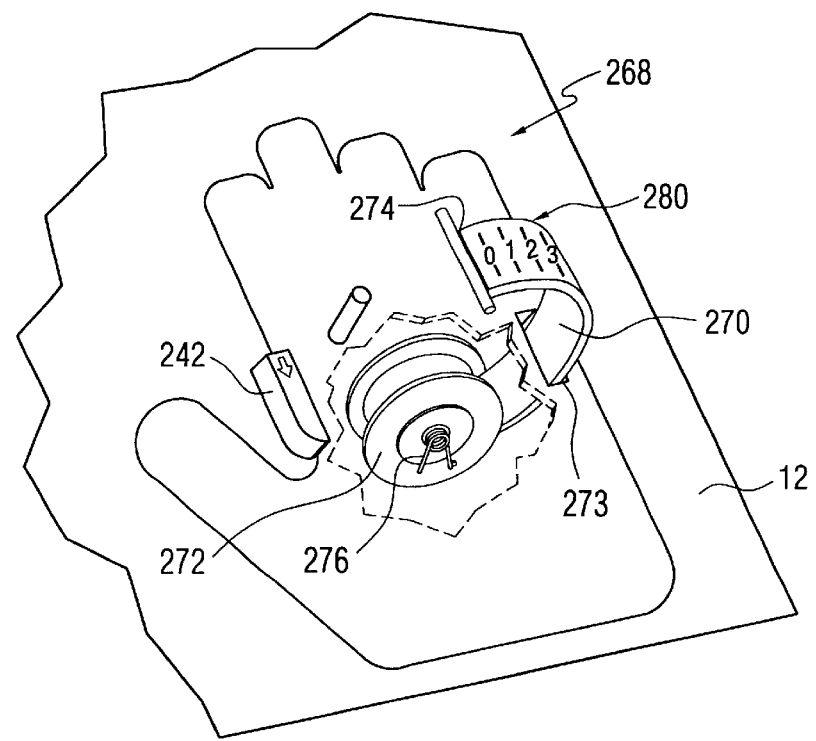
FIG. 8 is a partial, perspective view of a fourth embodiment of the right-hand measuring station according to the present invention; wherein a portion of the station is broken away for clarity.

Referring to FIG. 8, yet another embodiment of the girth measurement device 268 is shown. The device 268 includes a measuring tape 270 with a girth scale 280 thereon. A first end 288 of the measuring tape 270 is secured about a spool 272 rotatably mounted to the platform, beneath the surface of the platform 12. A portion of tape 272 extends through a slot 273 defined through the platform 12 so that a free end 274 of the tape is formed above the platform. The girth measurement device 268 also includes a biasing element, such as a coil spring 276, operatively associated with the spool and to bias the tape 270 from an unwound state to a wound state. When a user is not exerting a pulling force on the free end 274 of the tape 270, the tape returns to the wound state. In all other respects, the tape 272 measures a girth value similar to the embodiment previously discussed with FIGS. 3 and 5.

In another embodiment, the spool can be disposed above the platform 12 in, for example a stop member 242 adjacent the user's hand. In yet another embodiment, another type of biasing element such as a leaf spring or the like can be used. Furthermore, the association between the biasing element and the platform can be modified as know by those of ordinary skill in the art to bias the tape into the wound state.

Referring to FIGS. 1 and 9, sizing grid 18 is disposed on the upper surface 26 of the platform 12 between the hand measuring station 14 and 16. The grid 18 correlates a preferred finger length value and a selected palm girth value with a particular glove size or a selected range of glove sizes. FIG. 9 shows one non-limiting example of grid 18. In sizing grid 18, a series of palm girth values 92 and a series of preferred finger length values 94 define a matrix including of a plurality of areas 96.

The values 92 correspond to the marks 82 (see FIG. 6) on the girth scale 80. The values 94 correspond to the marks 53 and 54 (see FIG. 3) on the finger scales 50 and 52. Each area 96 corresponds to at least one glove size. The location of each area 96 is defined by a first coordinate corresponding to the assigned preferred finger length value and a second coordinate corresponding to the selected palm girth value.

In sizing grid 18, three sizes women's, cadet, and men's are shown. Within each size there are the categories of small, medium, medium-large, large, extra-large, and extra-extra-large. S represents small. M represents medium. ML represents medium-large. L represents large. XL represents extra-large. XXL represents extra-extra-large.

Referring to FIG. 2, although the grid 18 is shown mounted on the platform 12, it can be located elsewhere on the device 10 or be separate from the platform 12. Obviously, a chart or size grid 18 correlating finger lengths and palm girth values could be structured in a variety of ways to convey similar information. Additionally, other nomenclature may be used to define aspects of glove sizes, such as, for example, regular, cadet, and short.

Referring to FIG. 3, during use, a user places their right-hand 2 (shown in phantom) on platform 12 so that crotch 9b abuts stop member 28 and crotch 9a abuts thumb stop member 42. The user determines an index finger length value from the index finger scale 50, and a middle finger length value from the middle finger scale 52. If the tip end of a finger is located between two adjacent marks, the user should use the length value that is closest to the tip of the finger. The user notes the higher of the index and middle finger length values as a preferred finger length value.

As shown in FIG. 5, to measure a girth value of the hand 2, user draws free end of measuring tape 70 about the side of the hand 2 and over and across the top of the hand and the thumb stop 42 using tab 75, until a desired level of snugness is achieved. If a user desires a tight glove, the tape 70 can be pulled to maximum tightness. If the user desires a looser glove, the tape 70 can be pulled to less than maximum tightness. The user notes the palm girth value from the girth scale 80 on the tape that is aligned with the reference mark 86. The user repeats these steps for the left hand on the left-hand measuring station 16, shown in FIG. 2.

Then the user selects the largest of the preferred finger length values from each hand, and selects the larger girth value between the two girth values for each hand as the selected girth value. The user then refers to the sizing grid and correlates these values with the glove size with the aid of the sizing grid 18 (see FIG. 9). Thus, for example, for users with a selected palm girth value of 5 and a preferred finger length value of 3, the device 10 recommends the cadet medium glove size. In cases where the user is not satisfied with the recommended size, the user should then try on gloves in areas 96 adjacent to the recommended size. Thus, in the example above, if the cadet medium does not fit, the user should try a cadet small, a men's small, a men's medium, and a cadet medium-large.

The correlation between preferred finger length, girth, and the size of a properly fitting glove has been determined by precisely measuring the hands of at least three hundred golfers, and more preferably fifteen hundred golfers are measured, using a laser sizing system, averaging the results, and delineating the sizes according to the measurements. One recommended laser sizing system for taking such measurements is disclosed in U.S. Pat. No. 5,671,055. The preferred laser sizing system for taking such measurements is manufactured by Intelligent Automation Systems of Cambridge Mass. under the name 4DI Imager and used with a fixture and software as known by those of ordinary skill in the art.

Although two hands are measure preferably, in another embodiment only a single hand can be measured and the recommendation made from those preferred finger length and palm girth measurements.

EXAMPLE

In the non-limiting example below, referring to FIGS. 3 and 6, a glove fitting device 10 according to the present invention was constructed so that the marks 82 on the girth scale 80, and marks 53 and 54 on the finger scales 50 and 52 have the values shown in Table I.

TABLE I

GIRTH AND FINGER LENGTH SCALE VALUES

| Size Index | Palm Girth | Index Finger Length | Middle Finger Length |
|---|---|---|---|
| 0 | 19.685 cm or 7.75" | N/A | N/A |
| 1 | 20.32 cm or 8.0" | 6.477 cm or 2.55" | 7.493 cm or 2.95" |
| 2 | 20.955 cm or 8.25" | 6.858 cm or 2.7" | 7.874 cm or 3.1" |
| 3 | 21.59 cm or 8.5" | 7.112 cm or 2.8" | 8.128 cm or 3.2" |
| 4 | 22.225 cm or 8.75" | 7.366 cm or 2.9" | 8.382 cm or 3.3" |
| 5 | 22.86 cm or 9.0" | 7.62 cm or 3.0" | 8.636 cm or 3.4" |
| 6 | 23.495 cm or 9.25" | 7.874 cm or 3.1" | 8.89 cm or 3.5" |
| 7 | 24.13 cm or 9.5" | 8.128 cm or 3.2" | 9.144 cm or 3.6" |
| 8 | 24.765 cm or 9.75" | 8.382 cm or 3.3" | 9.398 cm or 3.7" |
| 9 | 25.4 cm or 10.0" | 8.636 cm or 3.4" | 9.652 cm or 3.8" |

For example, a hand with an absolute index finger length of 7.366 cm or 2.9" from reference point 28 (as shown in FIG. 3) is assigned an index finger length value of t. A hand with an absolute middle finger length of 7.874 cm from reference point 28 is assigned a middle finger length value of 2. The preferred finger length value is the larger of these values, thus 4, as discussed above. If the absolute palm girth of the same hand is 23.495 cm or 9.25", the hand is assigned a palm girth value of 6.

If the user's palm girth is 4 to 8, and the preferred finger length is less than the selected palm girth, the device recommends a cadet glove size. If the preferred finger length value and the selected palm girth value differ by more than two, the user should try on several gloves to determine the best compromise.

While it is apparent that the illustrative embodiments of the invention disclosed herein fulfill the objectives stated above, it is appreciated that numerous modifications and other embodiments may be devised by those skilled in the art. One such modification is that although reference is made to measuring the index and middle fingers, one of ordinary skill in the art understands that the invention herein is not limited to measuring the lengths of these fingers, but could readily be adapted to measuring the lengths or relative lengths of any combination of at least two digits. This is determined by the particular glove being fitted and the data available for delineating sizes. Another modification includes using a measurement system to measure the length of the fingers that includes movable gauges. The gauges are slidably mounted to the platform so that they slide along the longitudinal axis of the fingers. Each gauge can have length-indicating labels thereon or a pointer that points to labels on the platform. In addition, the embodiments above can modified so that some features of one embodiment are used with the features of another embodiment. The method can also be used with a laser sizing system that measures the length of two digits and girth and uses a sizing grid. Therefore, it will be understood that the appended claims are intended to cover all such modifications and embodiments which would come within the true spirit and scope of the present invention.

What is claimed is:

1. A hand measuring device for determining a glove size for a user with five digits, wherein the device comprises:
   a platform;

at least one measuring station associated with the platform including:
   a girth scale operatively associated with the platform for measuring a user's palm girth value;
   a first measuring system for measuring a first digit length value of a first digit of a user's hand; and
   a second measuring system for measuring a second digit length value of a second digit of the user's hand,
wherein the first digit length value is measured relative to a first position and the second digit length value is measured relative to a second position, and wherein the first position and the second position are located different distances from a reference point.

2. The hand measuring device of claim 1, wherein the reference point is a crotch between two of user's adjacent digits.

3. The hand measuring device of claim 1, wherein the first measuring system comprises a first digit scale including a plurality of spaced first marks for measuring the length of the first digit; and
   the second measuring system comprises a second digit scale including a plurality of spaced second marks for measuring the length of the second digit.

4. The hand measuring device of claim 3, where in the girth scale includes a plurality of spaced third marks.

5. The hand measuring device of claim 3, wherein there are nine first marks, nine second marks and ten third marks.

6. The hand measuring device of claim 3, further comprising:
   a first interval between at least two adjacent first marks that is different from a second interval between at least two remaining, adjacent first marks; and
   a third interval between at least two adjacent second marks is different from a fourth interval between at least two remaining, adjacent second marks.

7. The hand measuring device of claim 6, wherein the first interval is less than the second interval and the third interval is less than the fourth interval.

8. The hand measuring device of claim 7, wherein the first marks with the first interval are spaced further from a reference point than the first marks with second interval, and the second marks with the third interval are spaced further from the reference point than the second marks with the fourth interval.

9. The hand measuring device of claim 6, wherein a first distance is defined between a reference point and the first mark adjacent the reference point, and a second distance is defined between the reference point and the second mark adjacent the reference point, and the first distance is less than the second distance.

10. The hand measuring device of claim 1, further comprising a stop member configured to abut at least a portion of a crotch between two adjacent digits, when the user's hand is properly positioned on the measuring station.

11. The hand measuring device of claim 1, further comprising a first stop member configured to abut at least a portion of a first crotch between the first and second digits, and second stop member configured to abut at least a portion of a second crotch between the first digit and an adjacent, third digit.

12. The hand measuring device of claim 1, further comprising a grid associated with the platform for correlating a plurality of palm girth values and a plurality of preferred finger length values with a plurality of predetermined glove sizes.

13. The hand measuring device of claim 1, wherein the predetermined glove sizes comprise women's small, women's medium, women's medium-large, women's large, cadet small, cadet medium, cadet medium-large, cadet large, cadet extra-large, men's small, men's medium, men's medium-large, men's large, men's extra-large, men's extra-extra-large.

14. The hand measuring device of claim 1, further including a stripe of material fixed to the platform with the girth scale on one surface thereof.

15. The hand measuring device of claim 14, wherein the strip has one end connected to the platform, a spaced free end, and the girth scale is located between the two ends.

16. The hand measuring device of claim 14, wherein the strip has a central portion fixed to the platform and two free ends spaced therefrom, and the girth scale is located between the central portion and one end.

17. The hand measuring device of claim 1, further including
   a strip of material with the girth scale thereon;
   a spool rotatably coupled to the platform wherein a first end of the strip is secured to the spool; and
   a spring associated with the spool to bias the strip into a wound state, and upon exerting a pulling force on a second, free end of the tape at least a portion of the strip is in an unwound state.

18. The hand measuring device of claim 1, wherein the first digit is the index finger, and the second digit is the middle finger.

19. The hand measuring device of claim 18, wherein the reference point is a crotch between the index and middle fingers.

20. The hand measuring device of claim 1, further including at least two measuring stations, the first measuring station for measuring the user's right hand and the second measuring station for measuring the user's left hand.

21. A method for fitting gloves to a user, wherein the method comprises the steps of:
   measuring at least one hand of the user on a first scale to determine the girth of a palm of the user and assigning a girth value to that measurement;
   measuring the length of a first digit of at least one hand relative to a first position on a second scale and assigning a first digit length value thereto;
   measuring the length of a second digit of at least one hand relative to a second position on a second scale and assigning a second digit length value thereto;
   selecting the largest of the first digit length value or the second digit length value as a preferred digit length value; and
   recommending to the user a predetermined glove size based on the preferred digit length value and the girth value,
wherein the first position and the second position are located different distances from a reference point.

22. A method for fitting gloves to a user, wherein the method comprises the steps of:
   measuring both hands of the user on a first scale to determine the girth of a palm of the user and assigning a girth value to that measurement;
   measuring the length of a first digit of both hands relative to a first position and assigning first digit length values thereto;
   measuring the length of a second digit of both hands relative to a second position and assigning second digit length values thereto;
   assigning the greater of the first digit length values or the second digit length values as a preferred digit length value; and recommending to the user a predetermined glove size based on the preferred digit length value and the girth value, wherein the first position and the second position are located different distances from a reference point.

23. The method of claim 22, wherein the first digit is an index finger and the second digit is a middle finger.

24. The method of claim 22, further comprising recommending to the user a women's glove size, if the girth value is 3 or less.

25. The method of claim 22, further comprising recommending to the user a cadet or men's glove size, if the girth value is greater than 4.

26. The method of claim 22, further comprising recommending to the user:

fitting the user in gloves with a size of a women's small, when girth value is 0 and the preferred digit length value is 1;

fitting the user in gloves with the size of a women's medium when the girth value is 0 and the preferred digit length value is 2;

fitting the user in gloves with the size of a women's medium when the girth value is 1 and the preferred digit length value is 1 or 2;

fitting the user in gloves with the size of a women's medium-large when the girth value is 0 and the preferred digit length value is 3;

fitting the user in gloves with the size of a women's medium-large when the girth value is 1 and the preferred digit length value is 3 or 4;

fitting the user in gloves with the size of a women's medium-large when the girth value is 2 and the preferred digit length value is 2 or 3;

fitting the user in gloves with the size of a women's large when the girth value is 2 and the preferred digit length value is 4;

fitting the user in gloves with the size of a women's large when the girth value is 3 and the preferred digit length value is 2–4;

fitting the user in gloves with the size of cadet small when the girth value is 4 and the preferred digit length value is 2;

fitting the user in gloves with the size of a cadet small or men's small when the girth value is 4 and the preferred digit length value is 3;

fitting the user in gloves with the size of a men's small when the girth value is 4 and the preferred digit length value is 4 or 5;

fitting the user in gloves with the size of a men's medium when the girth value is 4 and the preferred digit length value is 6;

fitting the user in gloves with the size of a cadet medium when the girth value is 5 and the preferred digit length value is 3;

fitting the user in gloves with the size of a cadet medium when the girth value is 5 and the preferred digit length value is 3;

fitting the user in gloves with the size of a men's medium when the girth value is 5 and the preferred digit length value is 4, 5, or 6;

fitting the user in gloves with the size of a men's medium-large when the girth value is 5 and the preferred digit length value is 7;

fitting the user in gloves with the size of a cadet medium large when the girth value is 6 and the preferred digit length value is 4;

fitting the user in gloves with the size of a cadet medium-large or men's medium-large when the girth value is 6 and the preferred digit length value is 5;

fitting the user in gloves with the size of a men's medium when the girth value is 6 and the preferred digit length value is 6 or 7;

fitting the user in gloves with the size of a cadet large or men's large when the girth value is 7 and the preferred digit length value is 6;

fitting the user in gloves with the size of a men's large when the girth value is 7 and the preferred digit length value is 7 or 8;

fitting the user in gloves with the size of a cadet extra-large or men's extra-large when the girth value is 8 and the preferred digit length value is 7;

fitting the user in gloves with the size of a men's extra-large when the girth value is 8 and the preferred digit length value is 8 or 9; and fitting the user in gloves with the size of a men's extra-extra-large when the girth value is 9 and the preferred digit length value is 8 or 9.

* * * * *